United States Patent [19]

Herrnstadt et al.

[11] Patent Number: 4,764,372
[45] Date of Patent: Aug. 16, 1988

[54] COMPOSITIONS CONTAINING BACILLUS THURINGIENSIS TOXIN TOXIC TO BEETLES OF THE ORDER COLEOPTERA, AND USES THEREOF

[75] Inventors: Corinna Herrnstadt; George G. Soares, Jr., both of San Diego, Calif.

[73] Assignee: Mycogen Corporation, San Diego, Calif.

[21] Appl. No.: 714,790

[22] Filed: Mar. 22, 1985

[51] Int. Cl.$^4$ .................. C12R 1/07; A61K 37/02; A01N 63/00; A01N 25/12
[52] U.S. Cl. .................................. 424/93; 424/84; 435/832; 514/2
[58] Field of Search ............... 435/253, 68, 832; 424/84, 92, 93; 514/2

[56] References Cited

U.S. PATENT DOCUMENTS

| | | | |
|---|---|---|---|
| 3,086,922 | 4/1963 | Mechalas | 424/93 |
| 4,000,258 | 12/1976 | Shieh et al. | 424/93 |
| 4,565,695 | 1/1986 | Guss et al. | 424/84 |
| 4,695,455 | 9/1987 | Barnes et al. | 435/254 |
| 4,695,462 | 9/1987 | Barnes et al. | 424/195.1 |

OTHER PUBLICATIONS

Beegle, C. C. (1978) "Use of Entomogenous Bacteria in Agroecosystems," Developments in Indust. Microbiol. 20:97–104.
Couch, T. L. (1980) "Mosquito Pathogenicity of *Bacillus thuringiensis* var. *israelensis*," Dev. in Indust. Microbiol. 22:61–67.
Krieg, A. et al. (1983) *B. thuringiensis* var. *tenebrionis*; a new pathotype effective against Coleoptera larvae," Z. ang. Ent. 96:500–508. (In German and translated in English).
Lebrun, P., "Study of Synergetic Action of Chemical and Biological Insecticides on an Experimental Population of *Tenebrio molitor*", *Chemical Abstracts*, v. 87 N. 3 (1977) abst. 17260d.
Schuster, D. J.; "Adjuvants Tank-Mixed with *Bacillus thuringiensis* for Control of Cabbage Looper Larvae on Cabbage", *Biological Abstracts*, v. 68, N. 9, (1979); Ref. No. 53155.
Troitskaya, E. N.; "New Isolates of Entomopathogenic Crystal-forming Bacteria"; *Biological Abstracts*, v. 72, N. 11, (1981); Ref. No. 71160.
Cantwell, G. E. et al.; "Activity of the B-exotoxin of *Bacillus thuringiensis* var. *thuringiensis* Against the Colorado Potato Beetle", *Biological Abstracts*, v. 77, N. 8 (4-15-1984), Ref. No. 58279.

*Primary Examiner*—Elizabeth Weimar
*Attorney, Agent, or Firm*—Roman Saliwanchik; David R. Saliwanchik

[57] ABSTRACT

The subject invention concerns a novel and useful insecticide with activity against insect pests of the order Coleoptera. Pests in this order do heavy damage to crops, e.g., corn. The insecticide of the subject invention is a novel *B. thuringiensis* microbe given the specie designation M-7. The spores or crystal of this microbe are useful to control Coleoptera pests in various environments.

7 Claims, No Drawings

COMPOSITIONS CONTAINING BACILLUS THURINGIENSIS TOXIN TOXIC TO BEETLES OF THE ORDER COLEOPTERA, AND USES THEREOF

DESCRIPTION

BACKGROUND OF THE INVENTION

The spore-forming microorganism *Bacillus thuringiensis* (Bt) produces the best-known insect toxin. The toxin is a protein, designated as δ-endotoxin. It is synthesized by the Bt sporulating cell. The toxin, upon being ingested in its crystalline form by susceptible insect larvae, is transformed into biologically active moieties by the insect gut juice proteases. The primary target is insect cells of the gut epithelium, which are rapidly destroyed. Experience has shown that the activity of the Bt toxin is so high that only nanogram amounts are required to kill suseptible insect larvae.

The reported activity spectrum of Bt covers insect species within the order Lepidoptera, which is a major insect problem in agriculture and forestry. The activity spectrum also includes the insect order Diptera, wherein reside some species of mosquitoes and blackflies. See Couch, T. L., (1980) "Mosquito Pathogenicity of *Bacillus thuringiensis* var. *israelensis*," Developments in Industrial Microbiology 22, 61–67; Beegle, C. C., (1978) "Use of Entomogenous Bacteria in Agroecosystems," Developments in Industrial Microbiology, 20, 97–104.

Krieg et al., *Z. ang. Ent.* (1983) 96: 500–508, describe a Bt isolate named *Bacillus thuringiensis* var. *tenebrionis,* which is reportedly active against two beetles of the order Coleoptera. These are Colorado potato beetle, *Leptinotarsa decemlineata,* and *Agelastica alni.* This is the only known Bt isolate reported to contain such activity; all previously identified Bt strains have had activity against caterpillars (order Lepidoptera) or larvae of certain files (order Diptera).

The Krieg et al. Bt isolate is not available for sice-by-side comparison with the Bt isolate of the subject invention. Therefore, since the Krieg et al. Bt isolate is not available to the public, the Krieg et al. publication is not a valid patent law reference under U.S. law.

BRIEF SUMMARY OF THE INVENTION

Disclosed and claimed is a novel *Bacillus thuringiensis* isolate which, surprisingly, has activity against beetles of the order Coleoptera but not against *Trichoplusia ni, Spodoptera exigua* or *Aedes aegypti.* Included in the Coleoptera are various Diabrotica species (family Chrysomelidae) that are responsible for large agricultural losses. For example, *D. undecimpunctata* (western spotted cucumber beetle), *D. longicornis* (northern corn rootworm), *D. virgitera* (western corn rootworm), and *D. undecimpunctata howardi* (southern corn rootworm).

DETAILED DISCLOSURE OF THE INVENTION

The novel *Bacillus thuringiensis* isolate of the subject invention, designated "M-7," is unusual in having a unique parasporal body (crystal) which under phase contrast microscopy is dark in appearance with a flat, square configuration.

A subculture of *B thuringiensis* M-7 has been deposited in the permanent collection of the Northern Regional Research Laboratory, U.S. Department of Agriculture, Peoria, Ill., USA on Feb. 27, 1985. The culture was assigned the accession number NRRL B-15939 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

*B. thuringiensis* M-7, NRRL B-15939, can be cultured using standard art media and fermentation techniques. Upon completion of the fermentation cycle, the bacteria can be harvested by fist separating the Bt spores and crystals from the fermentation broth by means well known in the art. The recovered Bt spores and crystals can be formulated into a wettable powder, liquid concentrate, granules or other formulations by the addition of surfactants, dispersants, inert carriers and other components to facilitate handling and application for particular target pests. These formulation and application procedures are all well known in the art and are used with commercial strains of *B. thuringiensis* (HD-1) active against Lepidoptera, e.g., caterpillars.

Formulated products can be sprayed or applied onto foliage to control phytophagous beetles, or formulated bait granules containing an attractant and spores and crystals of Bt M-7 can be applied to the soil for control of soil-inhabiting Coleoptera. Formulated Bt M-7 can also be applied as a seed-coating or root treatment or total plant treatment.

Against Diabrotica larvae, which feed on the roots of corn, a bait granule containing cucurbitacin (a phagostimulant for diabroticite beetles derived from cucurbits) or other insect attractants and spores and crystals of Bt M-7 can be formulated. These granules can be planted in the row at planting. Also, a formulated product (wettable powder, etc.) can be sprayed directly on foliage to control susceptible adult beetles.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B. thuringiensis* M-7 NRRL B-15939

A subculture of *B. thuringiensis* M-7 NRRL B-15939 can be used to inoculate the following medium known as LB broth:

Tryptone: 10 gm
Yeast extract: 5 gm
NaCl: 5 gm
5N NaOH: 0.6 ml
Water: 1000 ml

As per standard microbiological techniques, the above medium would be sterilized prior to inoculation and the inoculation would be done using aseptic procedures.

A procedure that has produced good results is as follows:

A series of 150 ml Erlenmeyer flasks containing sterile PWYE medium (peptone 5.0%; yeast extract 0.1%; NaCl, 0.5% in 1 liter of water; adjust pH to 7.5) are inoculated from a petri plate culture of *B. thuringiensis* M-7, NRRL B-15939. The flasks are incubated at 30° C. on a rotary shaker (200 rpm) overnight. From this starter culture, 300 ml of LB broth in a 2 liter flask is inoculated using 7.5 ml of the starter. The LB-broth flasks are incubated under the same conditions as the starter, but are harvested after 4 days.

The above procedure can be readily scaled up to large fermentors by procedures well known in the art.

The Bt spores and crystals, obtained in the above fermentation, can be isolated by procedures well known in the art. A frequently-used procedure is to subject the harvested fermentation broth to separation techniqes, e.g., centrifugation.

EXAMPLE 2

Testing of B. thuringiensis M-7 NRRL B-15939 Sprores and Crystal

B. thuringiensis M-7 NRRL B-15939 spores and crystal, obtained as described above, were tested against various insects. The insect species tested and a summary of the results are listed below in Table 1.

TABLE 1

Summary of Effects of Bacillus thuringiensis Strain M-7 on Larvae of Several Insects

| Species | Common Name | Order | Stage Tested | Feeding Inhibition | Mortality |
| --- | --- | --- | --- | --- | --- |
| Trichoplusia ni | Cabbage Looper | Lepidoptera | L1 | — | — |
| Spodoptera exigua | Beet armyworm | Lepidoptera | L1 | — | — |
| Diabrotica undecimpunctata | Western spotted cucumber beetle | Coleoptera | L2 | + | + |
| Aedes aegypti | Yellow fever mosquito | Diptera | L1 | — | — |

The method used to test for D. undecimpunctata (WSCB) activity consisted of spraying a spore/crystal suspension onto leaf discs of lettuce in a spray tower apparatus. (The larvae of this species are reared on lettuce leaves.) The spray is dried in a laminar flow hood and placed in a container on moist filter paper. Ten larvae of WSCB are added and the containers are incubated at 25° C. and 14 hr photoperiod. Fresh treated discs are added as needed. Inhibition of feeding is noted and mortality is recorded at 5 and 7 days. Results of 2 bioassays are given in Table 2.

TABLE 2

Results of 2 Bioassays of Bacillus thuringiensis M-7 Against Second Instar Diabrotica undecimpunctata U. at 7 Days Post-Inoculation

| Treatment | Avg. no. leaf discs consumed/rep. | % Mortality |
| --- | --- | --- |
| Exp 1 | | |
| Control | 3 | 7.5 ± 15.0 |
| 4.3 × $10^7$ spores/ml | <1 | 27.5 ± 9.6 |
| 4.3 × $10^8$ spores/ml | 0 | 62.5 ± 26.3 |
| Exp 2 | | |
| Control | 1 | 12.5 ± 12.6 |
| 1 × $10^6$ spores/ml | <1 | 30.0 ± 8.2 |
| 1 × $10^7$ spores/ml | 0 | 50.0 ± 21.6 |

Recent tests have shown that B. thuringiensis M-7 NRRL B-15939 is also active against the yellow mealworm, Tenebrio molitor. This beetle is a specie of the family Tenebriondae, which is in the order Coleoptera.

We claim:

1. A process for controlling the insect pests Diabrotica undecimpunctata or Tenebrio molitor which comprises contacting said insect pests with an insect-controlling effective amount of B. thuringiensis M-7, having the identifying characteristics of NRRL B-15939.

2. A process, according to claim 1, wherein said insect pest is contacted with an insect-controlling effective amount of B. thuringiensis M-7, by incorporating said B. thuringiensis M-7 into a bait granule and placing said granule on or in the soil when planting seeds of a plant upon which plants said insect pests are known to feed.

3. A process for controlling Diabrotica undecimpunctata which comprises
   (1) preparing a bait granule comprising B. thuringiensis M-7 spores or crystals; and
   (2) placing said bait granule on or in the soil.

4. A process, according to claim 3, wherein said bait granule is applied at the same time corn seed is planted in the soil.

5. A composition of matter comprising B. thuringiensis M-7 spores or crystal in association with an insecticide carrier.

6. A composition of matter, according to claim 5, wherein said carrier comprises the beetle stimulant cucurbitacin or other attractants.

7. A composition of matter comprising B. thuringiensis M-7 spores or crystals in association with formulation ingredients suitable for use as a seed coating.

* * * * *

UNITED STATES PATENT AND TRADEMARK OFFICE
CERTIFICATE OF CORRECTION

PATENT NO. : 4,764,372

DATED : August 16, 1988

INVENTOR(S) : Corinna Herrnstadt, George G. Soares

It is certified that error appears in the above-identified patent and that said Letters Patent are hereby corrected as shown below:

| | |
|---|---|
| Column 1: | line 19: "suseptible" should read--susceptible--. |
| Column 2: | line 13: "fist" should read --first--. |
| Column 3: | line 15: "Sprores" should read --Spores--. |
| Claim 1: | line 3: "B. thuringiensis" should be italicized. |

Signed and Sealed this

Seventh Day of February, 1989

*Attest:*

DONALD J. QUIGG

*Attesting Officer*

*Commissioner of Patents and Trademarks*